US008106011B1

(12) United States Patent
Wong et al.

(10) Patent No.: US 8,106,011 B1
(45) Date of Patent: *Jan. 31, 2012

(54) METHOD FOR THE PREPARATION OF A HEAT STABLE OXYGEN CARRIER-CONTAINING COMPOSITION FACILATING BETA-BETA CROSS-LINKING

(75) Inventors: Bing Lou Wong, Irvine, CA (US); Sui Yi Kwok, Hong Kong (HK); Kwok Chu Butt, Hong Kong (HK)

(73) Assignee: Billion King International Limited, Kowloon (HK)

( * ) Notice: Subject to any disclaimer, the term of this patent is extended or adjusted under 35 U.S.C. 154(b) by 0 days.

This patent is subject to a terminal disclaimer.

(21) Appl. No.: 13/275,366

(22) Filed: Oct. 18, 2011

Related U.S. Application Data

(63) Continuation of application No. 13/225,797, filed on Sep. 6, 2011.

(60) Provisional application No. 61/529,279, filed on Aug. 31, 2011.

(51) Int. Cl.
*A61K 38/00* (2006.01)
*A61P 7/00* (2006.01)

(52) U.S. Cl. ................................ 514/13.5
(58) Field of Classification Search ................ None
See application file for complete search history.

(56) References Cited

U.S. PATENT DOCUMENTS

| | | |
|---|---|---|
| 4,529,719 A | 7/1985 | Tye |
| 4,543,209 A | 9/1985 | Tayot et al. |
| 4,598,064 A | 7/1986 | Walder |
| 4,600,531 A | 7/1986 | Walder |
| 4,831,012 A | 5/1989 | Estep |
| 4,987,048 A | 1/1991 | Shinozaki et al. |
| 5,084,558 A | 1/1992 | Rausch et al. |
| 5,189,146 A | 2/1993 | Hsia |
| RE34,271 E | 6/1993 | Walder |
| 5,250,665 A | 10/1993 | Kluger et al. |
| 5,296,465 A | 3/1994 | Rausch et al. |
| 5,344,393 A | 9/1994 | Roth et al. |
| 5,439,882 A | 8/1995 | Feola et al. |
| 5,451,205 A | 9/1995 | Roth et al. |
| 5,464,814 A | 11/1995 | Sehgal et al. |
| 5,591,710 A | 1/1997 | Hsia |
| 5,618,919 A | 4/1997 | Rausch et al. |
| 5,631,219 A | 5/1997 | Rosenthal et al. |
| 5,691,453 A | 11/1997 | Wertz et al. |
| 5,725,839 A | 3/1998 | Hsia |
| 5,741,893 A | 4/1998 | Hsia |
| 5,741,894 A | 4/1998 | Azari et al. |
| 5,753,616 A | 5/1998 | Rausch et al. |
| 5,767,089 A | 6/1998 | Hsia |
| 5,789,376 A | 8/1998 | Hsia |
| 5,804,561 A | 9/1998 | Hsia |
| 5,807,831 A | 9/1998 | Hsia |
| 5,811,005 A | 9/1998 | Hsia |
| 5,814,601 A | 9/1998 | Winslow et al. |
| 5,817,528 A | 10/1998 | Bohm et al. |
| 5,817,632 A | 10/1998 | Hsia |
| 5,824,781 A | 10/1998 | Hsia |
| 5,840,701 A | 11/1998 | Hsia |
| 5,840,851 A | 11/1998 | Plomer et al. |
| 5,865,784 A | 2/1999 | Faithfull et al. |
| 5,895,810 A | 4/1999 | Light et al. |
| 5,905,141 A | 5/1999 | Rausch et al. |
| 5,955,581 A | 9/1999 | Rausch et al. |
| 6,007,774 A | 12/1999 | Faithfull et al. |
| 6,054,427 A | 4/2000 | Winslow |
| 6,127,043 A | 10/2000 | Lange |
| 6,160,098 A | 12/2000 | Kerwin |
| 6,242,417 B1 | 6/2001 | Gerber et al. |
| 6,270,952 B1 | 8/2001 | Cook et al. |
| 6,288,027 B1 | 9/2001 | Gawryl et al. |
| 6,323,175 B1 | 11/2001 | Hsia |
| 6,399,357 B1 | 6/2002 | Winge |

(Continued)

FOREIGN PATENT DOCUMENTS

WO WO 89/12456 12/1989

OTHER PUBLICATIONS

Waks et al. Influence of Prosthetic Groups on Protein Folding and Subunit Assembly. The Journal of Biological Chemistry. Sep. 25, 1973, vol. 248, No. 18, pp. 6462-6470.*
Chatterjee et al. Isolation and Charactierzation of a New Hemoglobin Derivative Cross-linked between the alpha Chains (Lysine 99alpha1 -> Lysine 99alpha2). The Journal of Biological Chemistry, vol. 261, No. 21, pp. 9929-9937.*
Chatterjee et al. Mechanism for the Increase in Solubility of Deoxyhemoglobin S due to Cross-Linking the beta Chains between Lysine-82beta1 and Lysine-82-beta2. Biochemistry, 1982, vol. 21, pp. 5901-5909.*
Dragan et al. Bioelectrochemistry vol. 78 (2008) pp. 55-63.
Napolitano LM., "Hemoglobin-based oxygen carriers: first, second or third generation? Human or bovine? Where are we now?", Crit Care Clin. 25, 279-301 (2009).
Jiin-Yu Chen et al., "A review of blood substitutes: examining the history, clinical trial results, and ethics of hemoglobin-based oxygen carriers", Clinics 64(8), 803-813 (2009).

(Continued)

*Primary Examiner* — Marcela M Cordero Garcia
(74) *Attorney, Agent, or Firm* — Ella Cheong; Margaret Burke; Sam Yip

(57) ABSTRACT

Methods for preparation of a heat stable hemoglobin based oxygen-carrier-containing pharmaceutical composition such that beta-beta cross-linking is favored are provided. Using the methods of the present invention, the oxygen affinity of the resultant molecule can be controlled so that hemoglobin based oxygen carriers tailored for specific applications can be produced. Lower oxygen affinity crosslinked hemoglobin is useful for applications requiring rapid tissue oxygenation (e.g. hemorrhagic shock) while higher oxygen affinity cross-linked hemoglobin is useful for applications requiring a slower rate of oxygenation (e.g. cancer adjunct therapy). A highly purified and heat stable crosslinked non-polymeric tetrameric hemoglobin having beta-beta cross-linking of greater than 40-60% and suitable for use in mammals without causing renal injury and vasoconstriction is produced. A high temperature and short time (HTST) heat processing step is performed to effectively remove any undesired dimeric hemoglobin, non-crosslinked tetrameric hemoglobin, and plasma protein impurities.

12 Claims, 11 Drawing Sheets

U.S. PATENT DOCUMENTS

| | | | |
|---|---|---|---|
| 6,432,918 B1 | 8/2002 | Winslow |
| 6,486,306 B1 | 11/2002 | Winge |
| 6,506,725 B1 | 1/2003 | Rausch et al. |
| RE38,081 E | 4/2003 | Faithfull et al. |
| 6,566,504 B2 | 5/2003 | Bhattacharya et al. |
| 6,599,878 B2 | 7/2003 | Rooney |
| 6,610,832 B1 | 8/2003 | Gawryl et al. |
| 6,709,810 B2 | 3/2004 | Cook et al. |
| 6,740,139 B2 | 5/2004 | Russell et al. |
| 6,747,132 B2 | 6/2004 | Privalle et al. |
| 6,844,317 B2 | 1/2005 | Winslow et al. |
| 6,894,150 B1 | 5/2005 | Tye |
| 7,038,016 B2 | 5/2006 | Talarico et al. |
| 7,101,846 B2 | 9/2006 | Winslow |
| 7,293,985 B2 | 11/2007 | Cook et al. |
| 7,411,044 B2 | 8/2008 | Avella et al. |
| 7,435,795 B2 | 10/2008 | McGinnis et al. |
| 7,494,974 B2 | 2/2009 | Tye |
| 7,501,499 B2 | 3/2009 | Acharya et al. |
| 7,504,377 B2 | 3/2009 | Tye |
| 7,553,613 B2 | 6/2009 | Gawryl et al. |
| 7,625,862 B2 | 12/2009 | Winslow et al. |
| 7,655,392 B2 | 2/2010 | Stassinopoulos |
| 7,759,306 B2 | 7/2010 | Simoni et al. |
| 7,795,401 B2 | 9/2010 | Huang et al. |
| 7,932,356 B1 | 4/2011 | Wong et al. |
| 7,989,593 B1 | 8/2011 | Wong et al. |
| 2007/0142626 A1 | 6/2007 | Kluger et al. |

OTHER PUBLICATIONS

Lamy ML et al., "Randomized Trial of Diasbirin Cross-linked Hemoglobin Solution as an Alternative to Blood Transfusion alter Cardiac Surgery", Anesthesiology 92(3), 646-656 (2000).

Lois R. Manning et al., "Subunit dissociations in natural and recombinant hemoglobins", Protein Science 5(4), 775-781 (1996).

Ronald Kluger et al., "Protein-protein coupling and its application to functional red cell substitutes", Chem Commun (Camb). 46(8), 1194-1202 (2010).

Ronald Kluger, "Red cell substitutes from hemoglobin—do we start all over again?", Current Opinion in Chemical Biology 14(4), 538-543 (2010).

Kenji Sampei et al., "Role of nitric oxide scavenging in vascular response to cell-free hemoglobin transfusion ", Am J Physioi Heart Circ Physiol 289(3), H1191-H1201 (2005).

Tao Hu et al., "Preparation and characterization of dimeric bovine hemoglobin tetramers", Journal of Protein Chemistry 22(5), 411-416(2003).

Tao Hu et al., "PEGylation of Val-1(alpha) destabilizes the tetrameric structure of hemoglobin", Biochemistry 48(3), 608-616 (2009).

Kim D Vandegriff et al., "Hemospan: design principles for a new class of oxygen therapeutic", Artificial organs 33(2), 133-138 (2009).

Thoralf Kerner et al., "DCL-Hb for trauma patients with severe hemorrhagic shock: the European "On-Scene" multicenter study", Intensive Care Medicine 29(3), 378-385 (2003).

Chad R. Haney et al., "Purification and chemical modifications of hemoglobin in developing hemoglobin based oxygen carriers", Advanced Drug Delivery Reviews 40(3), 153-169 (2000).

Donat R. Spahn et al., "Artificial O2 carriers : Status in 2005", Current pharmaceutical design 11(31), 4099-4114 (2005).

Andre F. Palmer et al., "Tangential flow filtration of hemoglobin", Biotechnol Prog. 25(1), 189-199 (2009).

David C. Irwin et al., "Polymerized bovine hemoglobin decreases oxygen delivery during normoxia and acute hypoxia in the rat", Am J Physiol Heart Circ Physiol 295(3), H1090-H1099 (2008).

Guoyong Sun et al, "Preparation of Ultrapure Bovine and Human Hemoglobin by Anion Exchange Chromatography", J Chromatogr B Analyt Technol Biomed Life Sci. 867(1), 17 (2008).

Yiping Jia et al., "Effects of cross-linking and zero-link polymerization on oxygen transport and redox chemistry of bovine hemoglobin", Biochimica et Biophysica Acta 1794(8), 1234-1242 (2009).

Cai Jin et al., "Chemically Modified Porcine, Hemoglobins and Their Biological Properties", Protein and Peptide Letters, vol. 11, No. 4, 353-360 (2004).

Malavalli, J. of Protein Chemistry, vol, 19, No. 4, 2000, pp. 255-267.

Hu, Biochem. J. vol. 402, 2007, pp. 143-151.

Jones, J. of Biological Chemistry, vol. 271, No. 2, 1996, pp. 675-68O.

Chatterjee, J. of Biological Chemistry, vol. 261, No. 21, 1986, pp. 9929-9937.

Ji Proteins: Structure, Function, and Genetics, vol. 30, 1998, pp. 309-320.

Kavanugh, Biochemistry, vol. 27, 1988, pp. 1804-1808.

Kwansa, Proteins: Structure, Function, and Genetics, vol. 39, 2000, pp. 166-169.

Manning, Proc. Nat'l Acad. Sci. USA, vol. 88, 1991, pp. 3329-3333.

Snyder, Proc, Nat'l Acad. Sci. USA, vol. 84, 1987, pp. 7280-7284.

Felice D'Agnillo et al., "Site-specific modifications and toxicity of blood substitutes. The case of diaspirin cross-linked hemoglobin.", Advanced Drug Delivery Reviews 40, 2000, pp. 199-212.

Andre F. Palmer et al., "Small-Volume Resuscitation From Hemorrhagic Shock Using High-Molecular-Weight Tense-State Polymerized Hemoglobins", The Journal of TRAUMA, Feb. 17, 2011, pp. 1-10.

Sam-Yong Park et al., "Crystal Structures of Unliganded and Half-Liganded Human Hemoglobin Derivatives Cross-Linked between Lys 82β1 and Lys 82β2" Biochemistry 43, 2004, pp. 8711-8717.

Sirnona A. Dragan et al., "Spectroelectrochemical study of hemoglobin A, alpha- and beta-fumarate crosslinked hemoglobins; implications to autoxidation reaction", Bioelectrochemistry 73, 2008, pp. 55-63.

Clara Fronticelli et al., "Bovine hemoglobin as a potential source of hemoglobin-based oxygen carriers: crosslinking with bis (2,3-dibromosalycyl) fumarate", Biochimica et Biophysica Acta 874, 1986, pp. 76-81.

Clara Fronticelli et al., "Bovine hemoglobin pseudo-crosslinked with mono (3,5-dibromosalicyl)—fumarate", Eur. J. Biochem. 193, 1990, pp. 331-336.

Maurizio Marta et al., "Bovine Hemoglobin Cross-Linked through the β Chains: functional and structural aspects.", The Journal of Biological Chemistry, vol. 271, No. 13, 1996, pp. 7473-7478.

\* cited by examiner (a) No heat treatment (b) Heat-treated (90°C for 45 sec – 2 min or 80°C for 30 min), stabilized crosslinked tetrameric hemoglobin A) Native bovine hemoglobin
B) Hemoglobin crosslinked with DBSF under deoxygenated condition

METHOD FOR THE PREPARATION OF A HEAT STABLE OXYGEN CARRIER-CONTAINING COMPOSITION FACILATING BETA-BETA CROSS-LINKING

CROSS-REFERENCE TO RELATED APPLICATIONS

The present application is a continuation application of U.S. patent application Ser. No. 13/225,797 filed Sep. 6, 2011 which claims priority to provisional U.S. Patent Application No. 61/529,279 filed Aug. 31, 2011, the disclosure of which is incorporated by reference herein.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the processes, experiments, and data as described below and in the drawings attached hereto: Copyright© 2011, Billion King International Limited, All Rights Reserved.

TECHNICAL FIELD

The present invention relates to methods for the preparation of a heat stable oxygen-carrier-containing pharmaceutical composition such that beta-beta cross-linking is favored. Using the methods of the present invention, the oxygen affinity of the resulting molecule can be controlled so that hemoglobin based oxygen carriers tailored for specific applications can be produced. Lower oxygen affinity crosslinked hemoglobin is useful for applications requiring rapid tissue oxygenation (e.g. hemorrhagic shock) while higher oxygen affinity crosslinked hemoglobin is useful for applications requiring a slower rate of oxygenation (e.g. cancer adjunct therapy).

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Naturally-occurring hemoglobin is a tetramer which is generally stable when present within red blood cells. However, when naturally-occurring hemoglobin is removed from red blood cells, it becomes unstable in plasma and splits into two $\alpha$-$\beta$ dimers. Each of these dimers is approximately 32 kDa in molecular weight. These dimers may cause substantial renal injury when filtered through the kidneys and excreted. The breakdown of the tetramer linkage also negatively impacts the sustainability of the functional hemoglobin in circulation.

In order to solve the problem, recent developments in hemoglobin processing have incorporated various cross-linking techniques to create intramolecular bonds within the tetramer as well as intermolecular bonds between the tetramers to form polymeric hemoglobin. The prior art teaches that polymeric hemoglobin is the preferred form in order to increase circulatory half-life of the hemoglobin. However, as determined by the present inventors, polymeric hemoglobin more readily converts to met-hemoglobin in blood circulation. Met-hemoglobin cannot bind oxygen and therefore cannot oxygenate tissue. Therefore, the cross-linking taught by the prior art that causes the formation of polymeric hemoglobin is a problem. There is a need in the art for a technique that permits intramolecular cross-linking to create stable tetramers without the simultaneous formation of polymeric hemoglobin.

Further problems with the prior art attempts to stabilize hemoglobin include production of tetrameric hemoglobin that includes an unacceptably high percentage of dimer units (or non-crosslinked tetrameric hemoglobin that quickly dissociates to dimeric hemoglobin if administered to a patient); the presence of dimers makes the hemoglobin composition unsatisfactory for administration to mammals. The dimeric form of the hemoglobin can cause severe renal injury in a mammalian body; this renal injury can be severe enough to cause death. Therefore, there is a need in the art to create stable tetrameric hemoglobin with undetectable dimeric form in the final product.

Another problem with prior art hemoglobin products is a sudden increase in blood pressure following administration. In the past, vasoconstriction events have been recorded from older generation of hemoglobin based oxygen carriers. Thus there is a need in the art for a process to prepare hemoglobin which will not cause vasoconstriction and high blood pressure when applied to a mammal.

Further problems with prior art attempts to create stable hemoglobin include the presence of protein impurities such as immunoglobin G that can cause allergic effects in mammals. Therefore, there is a need in the art for a process which can produce stable tetrameric hemoglobin without protein impurities.

In addition to the above problems, there is a need in the art for stabilized tetrameric hemoglobin that is dimer free, phospholipid free and capable of production on an industrial scale.

Hemoglobin-based oxygen carriers can be used in a wide variety of medical applications; depending upon the medical application, different levels of oxygen affinity are desirable. For example, a hemoglobin molecule with low oxygen affinity can transfer oxygen more easily to a target tissue than a hemoglobin molecule with higher oxygen affinity. Therefore it would be desirable to control the oxygen affinity of the crosslinked tetrameric hemoglobin. Thus, there is a need in the art to control the type of cross-linking and cross-linking conditions to produce crosslinked tetrameric hemoglobin with precise levels of oxygen binding.

SUMMARY OF INVENTION

The present invention provides a method for processing a non-polymeric, heat stable purified crosslinked tetrameric hemoglobin suitable for use in mammals without causing severe renal injury, vascular detrimental effects and severe adverse events including death. The present invention removes the dimeric form of hemoglobin, non-crosslinked tetrameric hemoglobin, phospholipids and protein impurities. The present invention also provides a technique for controlling the oxygen affinity of the resultant crosslinked tetramer by controlling the type of cross-linking in the tetramer (e.g., the amount of beta-beta cross-linking, alpha-alpha cross-linking, alpha-beta cross-linking in the tetramer), the quaternary structure of tetramer, and the cross-linking conditions. Lower oxygen affinity crosslinked hemoglobin is useful for applications requiring rapid tissue oxygenation (e.g. hemorrhagic shock) while higher oxygen affinity crosslinked hemoglobin is useful for applications requiring a slower rate of oxygenation (e.g. cancer adjunct therapy). Additionally, the present invention uses (1) an instant cytolysis apparatus for precise and controlled hypotonic lysis, (2) a flowthrough column chromatography, (3) a high temperature short time (HTST) apparatus for heat processing the hemoglobin solution in the purification process to remove the undesirable non-stabilized dimers of hemoglobin and to remove the protein impurities, for example immunoglobin-G, so that renal injury, vascular detrimental effects and other toxicity reactions can be avoided, and (4) an air-tight infusion bag packaging to avoid oxygen intrusion into the final product.

The method includes a starting material of mammalian whole blood including at least red blood cells and plasma. Red blood cells are separated from the plasma in the mammalian whole blood followed by filtering to obtain a filtered red blood cell fraction. The filtered red blood cell fraction is washed to remove plasma protein impurities. The washed red blood cells are disrupted by a controlled hypotonic lysis for a time sufficient to lyse red blood cells without lysing white blood cells in an instant cytolysis apparatus. Filtration is performed to remove at least a portion of the waste retentate from the lysate. A first hemoglobin solution is extracted from the lysate.

One or more purification processes are performed on the hemoglobin solution such as ultrafiltration and/or chromatography.

The purified hemoglobin is crosslinked by bis-3,5-dibromosalicyl fumarate (DBSF) to form heat stable crosslinked hemoglobin without the formation of polymeric hemoglobin such that the molecular weight of the resultant non-polymeric crosslinked tetrameric hemoglobin is 60-70 kDa. The expression "non-polymeric" as used herein, refers to tetrameric hemoglobin that is not intermolecularly crosslinked with other hemoglobin molecules or any other non-hemoglobin molecules such as PEG. Depending upon the hemoglobin source, the quaternary structure of the hemoglobin and on the cross-linking conditions, a tetrameric product with a high percentage of beta-beta cross-linking can be produced. Further, the oxygen affinity of the resultant molecule can be controlled so that hemoglobin based oxygen carriers tailored for specific applications can be produced.

Following this procedure, the crosslinked hemoglobin is heat-treated to remove any residual non-crosslinked tetrameric hemoglobin and any non-stabilized hemoglobin, for example the dimeric form of hemoglobin, and any other protein impurities. Prior to the heat treatment N-acetyl cysteine is optionally added at a concentration of approximately 0.2% to the crosslinked tetrameric hemoglobin to prevent formation of met-hemoglobin. Immediately following heat treatment and cooling, N-acetyl cysteine is optionally added at a concentration of approximately 0.2% to 0.4% to further prevent formation of met-hemoglobin. The heat treatment is preferably a high temperature short time treatment conducted at approximately 70° C. to 95° C. for 30 seconds to 3 hours with subsequent cooling to 25° C. Any precipitates formed during the heat treatment are removed by centrifugation or filtration.

The dimer-free, phospholipid-free, protein impurities-free, heat stable, non-polymeric crosslinked tetrameric hemoglobin is then added to a pharmaceutically acceptable carrier.

Thereafter, the heat stable, crosslinked tetrameric hemoglobin is formulated and packaged in a custom-made and air-tight polyethylene, ethylene-vinyl-acetate, and ethylene-vinyl alcohol (PE, EVA, EVOH) infusion bag. The packaging prevents oxygen contamination which results in the formation of inactive met-hemoglobin.

DETAILED DESCRIPTION OF INVENTION

Figure 1:
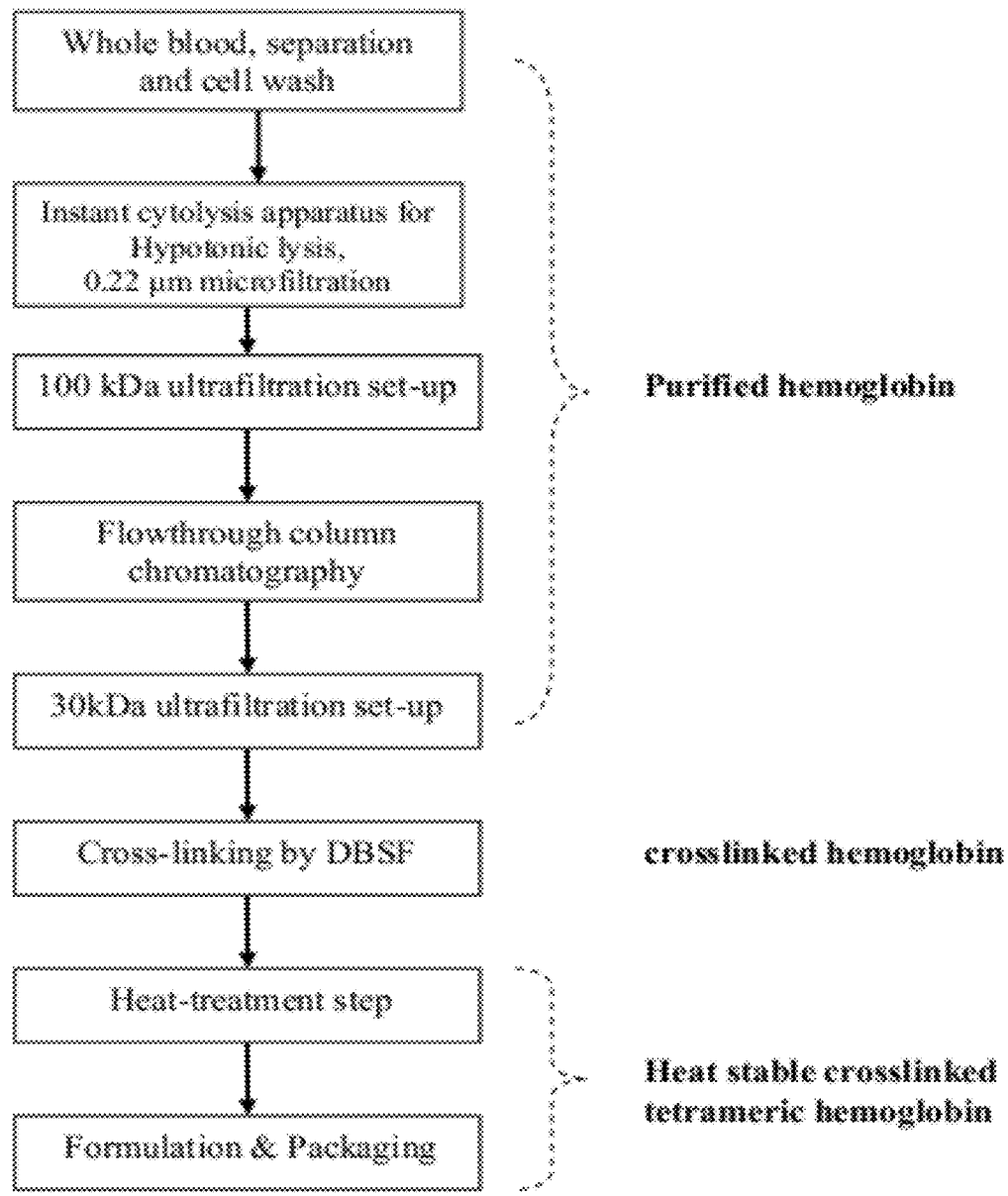
FIG. 1 is a flow-chart depicting an overview of a process of the present invention.

Hemoglobin is an iron-containing oxygen-transport protein in red blood cells of the blood of mammals and other animals. Hemoglobin exhibits characteristics of both the tertiary and quaternary structures of proteins. Most of the amino acids in hemoglobin form alpha helices connected by short non-helical segments. Hydrogen bonds stabilize the helical sections inside the hemoglobin causing attractions within the molecule thereto folding each polypeptide chain into a specific shape. A hemoglobin molecule is assembled from four globular protein subunits. Each subunit is composed of a polypeptide chain arranged into a set of α-helix structural segments connected in a "myoglobin fold" arrangement with an embedded heme group.

The heme group consists of an iron atom held in a heterocyclic ring, known as a porphyrin. The iron atom binds equally to all four nitrogen atoms in the center of the ring which lie in one plane. Oxygen is then able to bind to the iron center perpendicular to the plane of the porphyrin ring. Thus a single hemoglobin molecule has the capacity to combine with four molecules of oxygen.

In mammals, the most common type of hemoglobin is a tetramer; in humans, it is called hemoglobin A and consists of two α and two β non-covalently bound subunits designated as α2β2, each made of 141 and 146 amino acid residues respectively. The size and structure of α and β subunits are very similar to each other. Each subunit has a molecular weight of about 16 kDa for a total molecular weight of the tetramer of about 65 kDa. The four polypeptide chains are bound to each other by salt bridges, hydrogen bonds and hydrophobic interaction. The structure of bovine hemoglobin is similar to human hemoglobin (90.14% identity in α chain; 84.35% identity in β chain). The difference is the two sulfhydryl groups in the bovine hemoglobin positioned at β Cys 93, while the sulfhydryls in human hemoglobin are at positioned at α Cys 104, β Cys 93 and β Cys 112 respectively. Human hemoglobin shares high similarity with bovine, canine, porcine and equine hemoglobin when comparing their amino acid sequences.

In naturally-occurring hemoglobin inside the red blood cells, the association of an α chain with its corresponding β chain is very strong and does not disassociate under physiological conditions. However, the association of one αβ dimer with another αβ dimer is fairly weak outside red blood cells. The bond has a tendency to split into two αβ dimers each approximately 32 kDa. These undesired dimers are small enough to be filtered by the kidneys and be excreted, with the result being potential renal injury and substantially decreased intravascular retention time.

Therefore, it is necessary to stabilize any hemoglobin that is used outside of red blood cells both for efficacy and safety. The process for producing the stabilized hemoglobin is outlined below; an overview of the process of the present invention is presented in the flow chart of FIG. 1.

Initially, a whole blood source is selected as a source of hemoglobin from red blood cells. Mammalian whole blood is selected including, but not limited to, human, bovine, porcine, equine, and canine whole blood. The red blood cells are separated from the plasma, filtered, and washed to remove plasma protein impurities.

Figure 2:
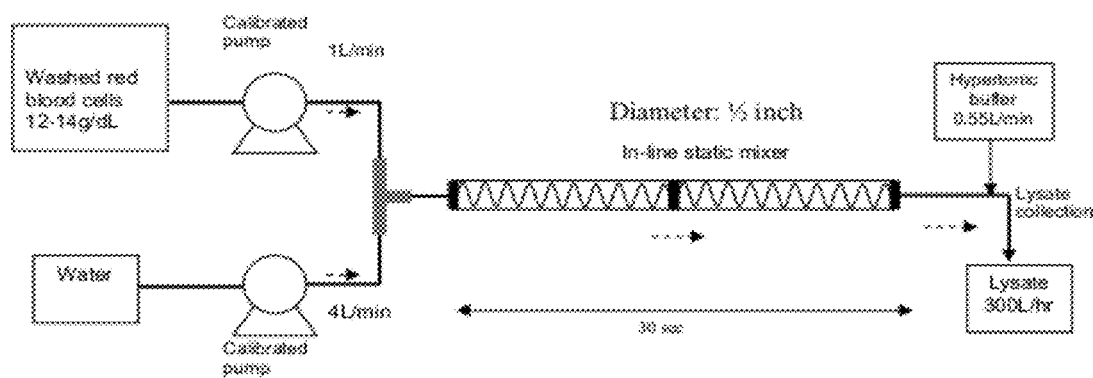
FIG. 2 schematically depicts an instant cytolysis apparatus used in the process of the present invention.

In order to release the hemoglobin from the red blood cells, the cell membrane is lysed. Although various techniques can be used to lyse red blood cells, the present invention uses lysis under hypotonic conditions in a manner which can be precisely controlled at volumes suitable for industrial-scale production. To this end, an instant cytolysis apparatus as seen in FIG. 2 is used to lyse the red blood cells. Hypotonic lysis creates a solution of lysate including hemoglobin and a waste retentate. To enable industrial-scale production, the lysis is carefully controlled such that only red blood cells are lysed without lysing white blood cells or other cells. In one embodiment, the size of the instant cytolysis apparatus is selected such that the red blood cells traverse the apparatus in 2 to 30 seconds or otherwise a time sufficient to lyse the red blood cells and preferably, 30 seconds. The instant cytolysis apparatus includes a static mixer. Deionized and distilled water is used as a hypotonic solution. Of course it is understood that the use of other hypotonic solutions having different saline concentrations would result in different time periods for red blood cell lysis. Because the controlled lysis procedure lyses the red blood cells only, not white blood cells or cellular matter, it minimizes the release of toxic proteins, phospholipids or DNA from white blood cells and other cellular matter. A hypertonic solution is added immediately after 30 seconds, that is, after the red blood-cell containing solution has traversed the static mixer portion of the instant cytolysis apparatus. The resultant hemoglobin has a higher purity and lower levels of contaminants such as undesired DNA and phospholipids resulted from hemoglobin than using other lysis techniques. Undesired nucleic acids from white blood cells and phospholipids impurities are not detected in the hemoglobin solution by polymerase chain reaction (detection limit=64 pg) and high performance liquid chromatography (HPLC, detection limit=1 µg/ml) method respectively.

At this stage in the process, the hemoglobin solution is purified to remove various protein and other impurities. This purification can be ultrafiltration based, chromatography based, or a combination of one or more ultrafiltration and/or chromatography processes. In an exemplary embodiment, two ultrafiltration processes are performed: one which removes impurities having molecular weights greater than hemoglobin before flowthrough column chromatography, and another which removes impurities having molecular weights less than hemoglobin after flowthrough column chromatography. The latter ultrafiltration process concentrates the hemoglobin. In some embodiments, a 100 kDa filter is used for the first ultrafiltration, while a 30 kDa filter is used for the second ultrafiltration.

Flowthrough column chromatography is used to remove protein impurities in the purified hemoglobin solution such as immunoglobin-G, albumin and carbonic anhydrase. In some embodiments, column chromatography is carried out by using one or a combination of commercially available ion exchange columns such as a DEAE column, CM column, hydroxyapatite column, etc. The pH for column chromatography is typically from 6 to 8.5. In one embodiment, a flowthrough CM column chromatography step is used to remove protein impurities at pH 8.0. Enzyme-linked immunosorbent assay (ELISA) and HPLC method are performed to detect the protein impurities and phospholipids remaining in the sample after elution from the column chromatography. This unique flowthrough column chromatography separation enables a continuous separation scheme for industrial-scale production. The ELISA result shows that the amount of these impurities is substantially low in the eluted hemoglobin (immunoglobin-G: 44.3 ng/ml; albumin: 20.37 ng/ml; carbonic anhydrase: 81.2 µg/ml). The protein impurities removal results using different kinds of columns with different pH values are shown in Table 1 below.

TABLE 1

| Column (pH condition) | Removal percentage (%) | | |
|---|---|---|---|
| | Carbonic anhydrase | Albumin | Immunoglobin-G |
| DEAE (at pH 7.5) | — | 68 | 29.8 |
| DEAE (at pH 7.8) | — | 60 | 50.9 |
| CM (at pH 6.2) | — | 32 | 21.8 |
| CM (at pH 8.0) | 5.6 | 53.2 | 66.4 |
| Hydroxyapatite (at pH 7.5) | 4.5 | 23.5 | 22.8 |

Following the column chromatographic process, the hemoglobin is subjected to cross-linking by DBSF. The conditions are selected such that cross-linking occurs between the beta-beta subunits is favored and the resultant product has greater than 50% beta-beta cross-linking. For cross-linking under deoxygenated condition, the resulting hemoglobin has a low oxygen affinity with a higher p50 value compared with the native hemoglobin of the same species measured under substantially similar conditions. For example, for bovine hemoglobin, the native bovine hemoglobin has a p50 value on the order of 23-29 mm Hg. The crosslinked bovine hemoglobin formed under deoxygenated conditions in the present invention has a p50 value on the order of 38-50 mm Hg. Lower oxygen affinity means that the tetramer can "offload" oxygen to a target more easily than a material with a higher oxygen affinity. For cross-linking of bovine hemoglobin under oxygenated conditions, a material with a higher oxygen affinity is formed with a lower p50 value, less than approximately 23 mm Hg, compared with native bovine hemoglobin which has a p50 value on the order of 23-29 mm Hg. Lower oxygen affinity compositions are used when rapid oxygenation is desired as in cases of tissue hypoxia resulting from extensive blood loss (e.g., hemorrhagic shock). Higher oxygen affinity compositions are useful for oxygenation adjunct therapies in cancer treatment where a slower delivery rate of oxygen is desirable.

For human hemoglobin, cross-linking under deoxygenated condition typically produces a majority of alpha-alpha crosslinked hemoglobin with lower oxygen affinity, that is, an oxygen affinity that is decreased on the order of at least 2-fold from native human hemoglobin. Cross-linking under oxygenated conditions tends to favor production of beta-beta crosslinked hemoglobin with a higher oxygen affinity (that is, a lower p50, less than approximately 23 mm Hg), compared with the native human hemoglobin under the same condition (a p50 value on the order of approximately 23-30 mm Hg).

For deoxygenated cross-linking condition preferably less than 0.1 ppm dissolved oxygen level, it is maintained with a molar ratio of hemoglobin to DBSF from 1:2.5 to 1:4.0 for a period of time from 3 to 16 hours at ambient temperature (15-25° C.), at a pH of preferably around 8-9. The resultant crosslinked hemoglobin is tetrameric hemoglobin having a molecular weight of 60-70 kDa, demonstrating that polymeric hemoglobin is not present. The yield of the DBSF reaction is high, >99% and the dimer concentration in the final product is low. Optionally, the present process does not require sulfhydryl treatment reagents such as iodoacetamide to react with the hemoglobin before cross-linking as used in various prior art processes. For cross-linking under oxygenated conditions, an oxygenated environment (such as air, $pO_2$ is around 149 mmHg; or pure $O_2$, $pO_2$ is nearly 760 mmHg) is used while the remaining conditions above are substantially the same.

For bovine hemoglobin, the beta-beta cross-linking is greater than 50%, and preferably greater than 60% for cross-linking under deoxygenated conditions (less than 0.1 ppm dissolved oxygen level). For bovine hemoglobin crosslinked under oxygenated condition, beta-beta cross-linking is also favored, typically at a level greater that 40% beta-beta crosslinking.

For human hemoglobin, cross-linking under oxygenated conditions favors beta-beta cross-linking.

Following cross-linking, phosphate buffered saline (PBS), a physiological buffer, is exchanged for the cross-linking solution and any residual chemicals are removed by tangential flow filtration.

Following cross-linking, the present invention provides a heat processing step (High Temperature Short Time, HTST) for the crosslinked tetrameric hemoglobin solution. The heat treatment takes place in a deoxygenated environment. Prior to heat treatment, N-acetyl cysteine is optionally added to prevent formation of met-hemoglobin (inactive hemoglobin). After the heat processing step, the solution is cooled and N-acetyl cysteine is optionally added to maintain a low level of met-hemoglobin. If N-acetyl cysteine is added before and after heat treatment, the amount added before heat treatment is approximately 0.2%, while the amount added after heat treatment is approximately 0.2 to 0.4%. However, if N-acetyl cysteine is added only after heat treatment, then the amount added is 0.4%.

In some embodiments, the crosslinked tetrameric hemoglobin solution is heated in a deoxygenated environment (less than 0.1 ppm dissolved oxygen level) under a range of temperatures from 50° C. to 95° C. for durations from 0.5 minutes to 10 hours. In some embodiments, the crosslinked tetrameric hemoglobin solution is heated under a range of temperatures from 70° C. to 95° C. and for durations from 30 seconds to 3 hours. In some preferred embodiments, the crosslinked tetrameric hemoglobin solution is heated under 80° C. for 30 minutes. And yet in other preferred embodiments, the crosslinked hemoglobin solution is heated to 90° C. for 30 seconds to 3 minutes, then rapidly cooled down to approximately 25° C. in approximately 15 to 30 seconds, and the N-acetyl cysteine is optionally added as set forth above.

Figure 3:
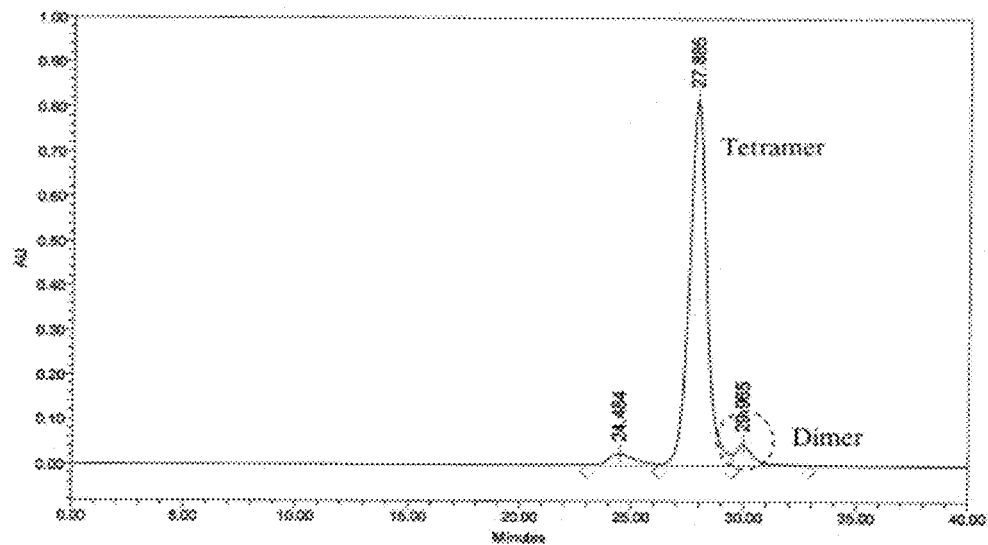
FIG. 3 depicts high performance liquid chromatography analysis for (a) non-heat treated crosslinked tetrameric hemoglobin, and (b) heat stable crosslinked tetrameric hemoglobin which has undergone a heat treatment at 90° C. for 45 seconds to 2 minutes or 80° C. for 30 minutes.
Figure 3:
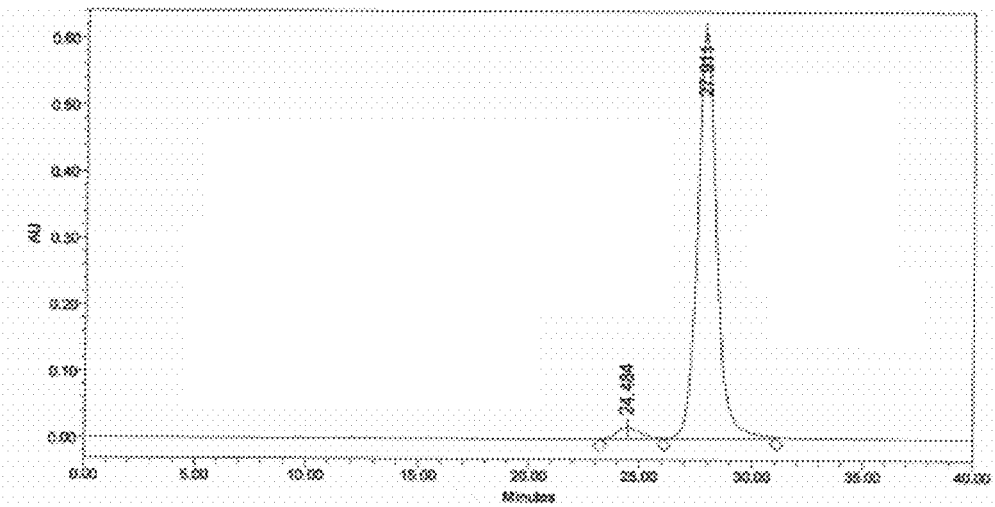

To analyze the outcome of the HTST heat processing step, a HPLC analytical method is used to detect the amount of dimer after this heat processing step. The mobile phase for HPLC analysis contains magnesium chloride (0.75M) which can separate dimer (non-stabilized tetramer) and heat stable crosslinked tetrameric hemoglobin. For promoting hemoglobin dissociation into dimers, magnesium chloride is approximately 30 times more effective than sodium chloride at the same ionic strength. The heat processing step also acts as a denaturation step to dramatically remove unwanted protein impurities in the crosslinked tetrameric hemoglobin (undetectable in immunoglobin-G; 96.15% decrease in albumin; 99.99% decrease in carbonic anhydrase). Enzyme-linked immunosorbent assay (ELISA) is performed to detect the protein impurities in the sample. Thus the purified, heat stable crosslinked tetrameric hemoglobin solution has an undetectable level of dimer (below detection limit: 0.043%), and immunoglobin-G, and a very low amount of albumin (0.02 μg/ml) and carbonic anhydrase (0.014 μg/ml). FIG. 3 shows that the dimeric form of hemoglobin is undetectable in a HPLC system. Table 2 shows the experimental results regarding the protein impurities and dimer removal by the HTST heat processing step. This HTST heat processing step enables the selective separation of heat stable crosslinked tetramer from unstable tetramer (e.g., non crosslinked tetramer) and dimer.

TABLE 2

| | Immuno-globin-G (μg/ml) | Albumin (μg/ml) | Carbonic anhydrase (μg/ml) | Tetramer (%) | Dimer (%) |
|---|---|---|---|---|---|
| No heat treatment | 0.36 | 0.57 | 355.41 | 90.1 | 5.4 |
| 80° C. for 10 min | Not detectable | 0.33 | 0.032 | 92.7 | 3.4 |
| 80° C. for 15 min | Not detectable | 0.14 | 0.022 | 93.3 | 2.9 |
| 80° C. for 30 min | Not detectable | 0.03 | 0.014 | 96.6 | Not detectable |
| No heat treatment | 0.29 | 0.52 | 261.80 | 91.8 | 5.3 |
| 90° C. for 1.0 min | Not detectable | 0.21 | >0.063 | 93.4 | 2.0 |
| 90° C. for 1.5 min | Not detectable | 0.04 | 0.022 | 94.9 | 0.6 |
| 90° C. for 2.0 min | Not detectable | 0.02 | 0.016 | 96.1 | Not detectable |

Following the heat processing step for the crosslinked hemoglobin under a deoxygenated condition, the heat stable crosslinked tetrameric hemoglobin is ready for pharmaceutical formulation and packaging. The present invention describes an air-tight packaging step of the heat stable crosslinked tetrameric hemoglobin solution in a deoxygenated environment. Heat stable crosslinked tetrameric hemoglobin in the present invention is stable when maintained in a deoxygenated condition for more than two years.

In this invention, the oxygen carrier-containing pharmaceutical composition is primarily intended for intravenous injection application. Traditionally, prior products use conventional PVC blood bag or Stericon blood bag which has high oxygen permeability which will eventually shorten the life span of the product since it turns into inactive met-hemoglobin rapidly (within a few days) under oxygenated conditions.

The packaging used in the present invention results in the heat stable crosslinked tetrameric hemoglobin being stable for more than two years. A multi-layer package of EVA/EVOH material is used to minimize the gas permeability and to avoid the formation of inactive met-hemoglobin. A 100 ml infusion bag designed for use with the purified and heat stable crosslinked tetrameric hemoglobin of the present invention is made from a five layers EVA/EVOH laminated material with a thickness of 0.4 mm that has an oxygen permeability of 0.006-0.132 $cm^3$ per 100 square inches per 24 hours per atmosphere at room temperature. This material is a Class VI plastic (as defined in USP<88>), which meets the in-vivo Biological Reactivity Tests and the Physico-Chemical Test and is suitable for fabricating an infusion bag for intravenous injection purpose. This primary bag is particularly useful to protect the heat stable crosslinked tetrameric hemoglobin solution from long term oxygen exposure that causes its instability and eventually affects its therapeutic properties.

For secondary protection of blood products, it has been known to use aluminum overwrap to protect against potential air leakage and to maintain the product in a deoxygenated state. However, there is a potential of pin holes in the aluminum overwrap that compromises its air tightness and makes the product unstable. Therefore the present invention uses as secondary packaging an aluminum overwrap pouch which prevents oxygenation and also prevents light exposure. The composition of the overwrap pouch includes 0.012 mm of polyethylene terephthalate (PET), 0.007 mm of aluminum (Al), 0.015 mm of nylon (NY) and 0.1 mm of polyethylene (PE). The overwrap film has a thickness of 0.14 mm and an oxygen transmission rate of 0.006 $cm^3$ per 100 square inches per 24 hours per atmosphere at room temperature. This secondary packaging lengthens the stability time for the hemoglobin, extending the product shelf-life.

The process in this invention is applicable to large scale industrial production of the heat stable crosslinked tetrameric hemoglobin. In addition, the heat stable crosslinked tetrameric hemoglobin in combination with a pharmaceutical carrier (e.g. water, physiological buffer, in capsule form) is suitable for mammalian use.

The oxygen carrier-containing pharmaceutical composition of the present invention is useful in improving tissue oxygenation, in cancer treatment, in the treatment of oxygen-deprivation disorders such as hemorrhagic shock, and in heart preservation under a low oxygen content environment (e.g. heart transplant). In exemplary embodiments, the dosage is selected to have a concentration range of approximately 0.2-1.3 g/kg with an infusion rate of less than 10 ml/hour/kg body weight.

For the use in the treatment of oxygen-deprivation disorders and for heart preservation, the oxygen carrier-containing pharmaceutical composition with a lower oxygen affinity of the present invention serves as a blood substitute providing oxygen to a target organ. Lower oxygen affinity crosslinked hemoglobin is useful for applications requiring rapid tissue oxygenation (e.g. hemorrhagic shock and ex vivo organ preservation).

For applications in cancer treatment, the oxygen carrier-containing pharmaceutical composition with a higher oxygen affinity of the present invention serves as a tissue oxygenation agent to improve the oxygenation in tumor tissues, thereby enhancing chemo- and radiation sensitivity. A higher oxygen affinity hemoglobin is useful for applications requiring a slower rate of oxygenation (e.g. cancer adjunct therapy).

EXAMPLES

The following examples are provided by way of describing specific embodiments of this invention without intending to limit the scope of this invention in any way.

Example 1

Process Overview

A schematic flow diagram of the process of the present invention is illustrated in FIG. 1. Bovine whole blood is collected into an enclosed sterile container/bag containing 3.8% (w/v) tri-sodium citrate solution as anti-coagulant. Blood is then immediately mixed well with tri-sodium citrate solution to inhibit blood clotting. Red blood cells (RBC) are isolated and collected from plasma and other smaller blood cells by an apheresis mechanism. A "cell washer" is used for this procedure with gamma sterilized disposable centrifuge bowl. RBC are washed with an equal volume of 0.9% (w/v sodium chloride) saline.

Washed RBC are lysed to release hemoglobin content by manipulating hypotonic shock to the RBC cell membrane. A specialized instant cytolysis apparatus for RBC lysis device depicted in FIG. 2 is used for this purpose. Following RBC lysis, hemoglobin molecules are isolated from other proteins by tangential-flow ultrafiltration using a 100 kDa membrane. Hemoglobin in the filtrate is collected for flowthrough column chromatography and further concentrated to 12-14 g/dL by a 30 kDa membrane. Column chromatography is carried out to remove the protein impurities.

The concentrated hemoglobin solution is first reacted with DBSF to form heat stable crosslinked tetrameric hemoglobin molecules. A heat processing step is then performed under deoxygenated conditions at 90° C. for 30 seconds to three minutes before final formulation and packaging.

Example 2

Time & Controlled Hypotonic Lysis and Filtration

Bovine whole blood is freshly collected and transported under a cool condition (2 to 10° C.). The red blood cells are separated from the plasma via a cell washer and subsequently with a 0.65 μm filtration. After washing the red blood cells (RBC) filtrate with 0.9% saline, the filtrate is disrupted by hypotonic lysis. The hypotonic lysis is performed by using the instant cytolysis apparatus depicted in FIG. 2. The instant cytolysis apparatus includes a static mixer to assist in cell lysis. A RBC suspension with controlled hemoglobin concentration (12-14 g/dL) is mixed with 4 volumes of purified water to generate a hypotonic shock to RBC cell membranes. The period of hypotonic shock is controlled to avoid unwanted lysis of white blood cells and platelets. The hypotonic solution passes through the static mixer portion of the instant cytolysis apparatus for 2 to 30 seconds or otherwise a time sufficient to lyse the red blood cells and preferably, 30 seconds. The shock is terminated after 30 seconds by mixing the lysate with 1/10 volume of hypertonic buffer as it exits the static mixer. The hypertonic solution used is 0.1M phosphate buffer, 7.4% NaCl, pH 7.4. The instant cytolysis apparatus of FIG. 2 can process at 50 to 1000 liters of lysate per hour and, preferably at least 300 liters per hour in a continuous manner.

Following the RBC lysis, the lysate of red blood cells is filtered by a 0.22 μm filter to obtain a hemoglobin solution. Nucleic acids from white blood cells and phospholipids impurities are not detected in the hemoglobin solution by polymerase chain reaction (detection limit=64 pg) and HPLC (detection limit=1 μg/ml) method respectively. A first 100 kDa ultrafiltration is performed to remove impurities having a higher molecular weight than hemoglobin. A flowthrough column chromatography is followed to further purify the hemoglobin solution. A second 30 kDa ultrafiltration is then performed to remove impurities having a lower molecular weight than hemoglobin and for concentration.

Example 3

Viral Clearance Study on Stroma-Free Hemoglobin Solution

In order to demonstrate the safety of the product from this invention, the virus removal abilities of (1) 0.65 μm diafiltration step and (2) 100 kDa ultrafiltration step are demonstrated by virus validation study. This is done by the deliberate spiking of a down-scaled version of these two processes with different model viruses (encephalomyocarditis virus, pseudorabies virus, bovine viral diarrhea virus and bovine parvovirus). In this study, four types of viruses (see Table 3) are used. These viruses vary in their biophysical and structural features and they display a variation in resistance to physical and chemical agents or treatments.

TABLE 3

| Target Virus | Model Virus | Taxonomy | Genome | Structure | Size [nm] | Stability* |
|---|---|---|---|---|---|---|
| Hepatitis C virus | Bovine viral diarrhea virus (BVDV) | *Flaviviridae* | ssRNA | enveloped | 40-60 | low |
| — | Encephalomyocarditis virus (EMCV) | *Picornavirus* | ssRNA | non-enveloped | 25-30 | medium |
| Parvovirus B19 | Bovine parvovirus (BPV) | *Parvoviridae* | ssDNA | non-enveloped | 18-26 | very high |
| Hepatitis B virus | Pseudorabies virus (PRV) | *Herpesviridae* | dsDNA | enveloped | 120-200 | Low to medium |

The validation scheme is briefly shown in the following Table 4.

TABLE 4

| Diafiltration | Ultrafiltration |
|---|---|
| Cell Washing | Virus spiking |
| ↓ | ↓ |
| Virus spiking | Ultrafiltration |
| ↓ | ↓ |
| Diafiltration | Virus tests |
| ↓ | |
| Virus tests | |

The summary of the log reduction results of the 4 viruses in (1) 0.65 μm diafiltration and (2) 100 kDa ultrafiltration is shown in the following Table 5. All four viruses, BVDV, BPV, EMCV and PRV, are effectively removed by 0.65 μm diafiltration and 100 kDa ultrafiltration.

TABLE 5

| Viruses | BVDV | | BPV | | EMCV | | PRV | |
|---|---|---|---|---|---|---|---|---|
| Run | 1 | 2 | 1 | 2 | 1 | 2 | 1 | 2 |
| 0.65 μm Diafiltration | 2.69 | 3.20 | 3.73 | 3.53 | 3.25 | >3.90 | 2.67 | 2.63 |
| 100 kDa Ultrafiltration | ≧4.68 | ≧4.38 | 5.87 | 5.92 | 3.60 | 3.43 | ≧6.05 | 3.27 |
| Cumulative maximum | ≧7.88 | | 9.65 | | ≧7.50 | | ≧8.72 | |
| Cumulative minimum | ≧7.07 | | 9.40 | | 6.68 | | 5.90 | |

Annotation:
≧no residual infectivity determined

Example 4

Flowthrough Column Chromatography

Figure 4:
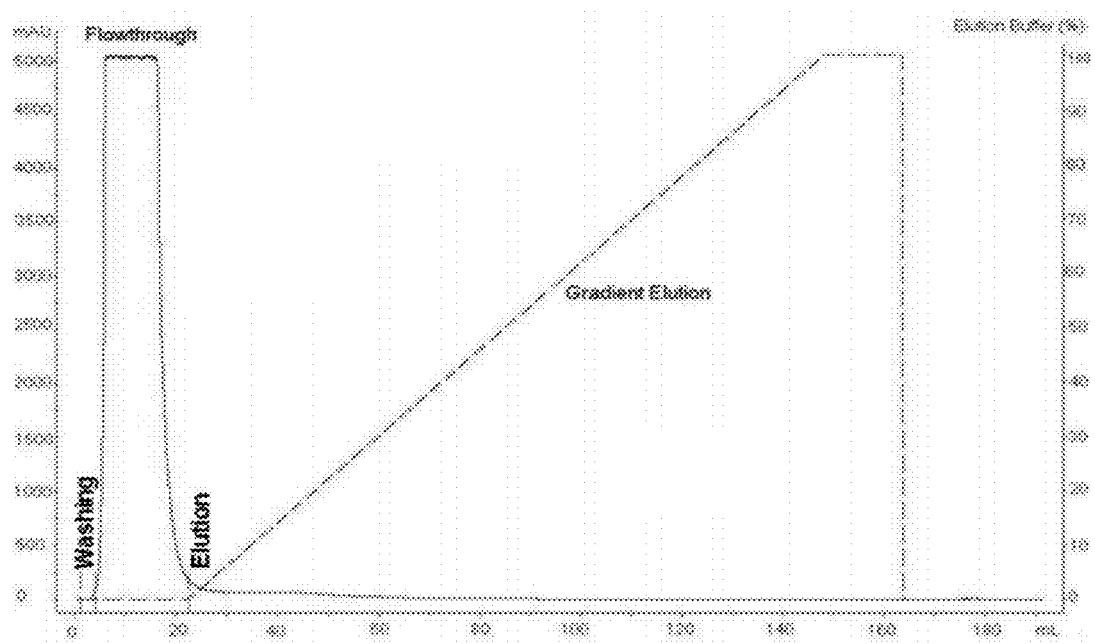
FIG. 4 is an elution profile for flowthrough column chromatography; the hemoglobin solution is in the flowthrough fraction.

A CM column (commercially available from GE healthcare) is used to further remove any protein impurities. The starting buffer is 20 mM sodium acetate (pH 8.0), and the elution buffer is 20 mM sodium acetate, 2M NaCl (pH 8.0). After the equilibration of the CM column with starting buffer, the protein sample is loaded into the column. The unbound protein impurities are washed with at least 5 column volume of starting buffer. The elution is performed using 25% elution buffer (0-0.5M NaCl) in 8 column volume. The elution profile is shown in FIG. 4; the hemoglobin solution is in the flowthrough fraction. The purity of the flowthrough fraction is analyzed by ELISA. The results are indicated in the following Table 6.

TABLE 6

| | Protein impurities | | |
|---|---|---|---|
| | Immuno-globin-G | Carbonic anhydrase | Albumin |
| Before CM column | 1320 ng/ml | 860.3 μg/ml | 435.2 ng/ml |
| Flowthrough (containing hemoglobin) | 44.3 ng/ml | 81.2 μg/ml | 20.4 ng/ml |

Figure 5:
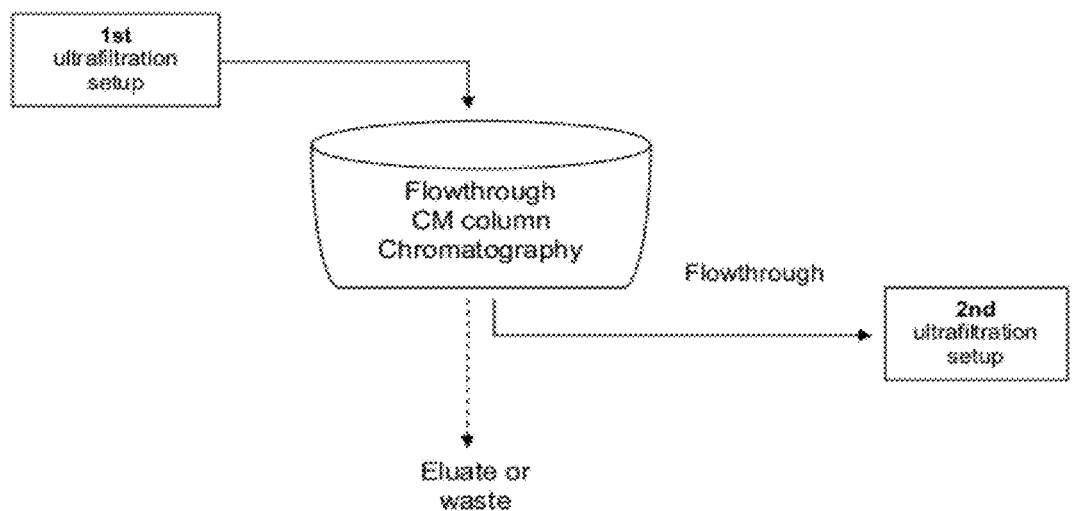
FIG. 5 schematically depicts a flowthrough CM column chromatography system with ultrafiltration for an industrial scale operation.

As the hemoglobin solution is in the flowthrough from the CM column chromatography at pH 8 (not in the eluate), it is a good approach for continuous industrial scale operation. The first ultrafiltration set-up is connected directly to the flowthrough CM column chromatography system, and the flowthrough tubing can be connected to the second ultrafiltration set-up for industrial scale operation. The schematic industrial process configuration is shown in FIG. 5.

Example 5

Preparation of Heat Stable Crosslinked Tetrameric Hemoglobin (5a) Cross-Linking Reaction with DBSF Under a Deoxygenated Condition The cross-linking reaction is carried out in a deoxygenated condition, that is, less than 0.1 ppm dissolved oxygen level. DBSF is added to the hemoglobin solution to form crosslinked tetrameric hemoglobin without formation of polymeric hemoglobin. DBSF stabilization procedure stabilizes the tetrameric form of hemoglobin (65 kDa) and prevents dissociation into dimers (32 kDa) which are excreted through the kidneys. In this embodiment, a molar ratio of hemoglobin to DBSF of 1:2.5 is used and the pH is 8.6. This process is carried out for a period of 3-16 hours at ambient temperature (15-25° C.) in an inert atmosphere of nitrogen to prevent oxidation of the hemoglobin to form ferric met-hemoglobin which is physiologically inactive (dissolved oxygen level maintained at less than 0.1 ppm). The completeness of DBSF reaction is monitored by measuring the residual DBSF using HPLC. The yield of the DBSF reaction is high, >99%. The production of beta-beta crosslinks is on the order of at least about 40%.

(5b) HTST Heat Processing Step

Figure 6:
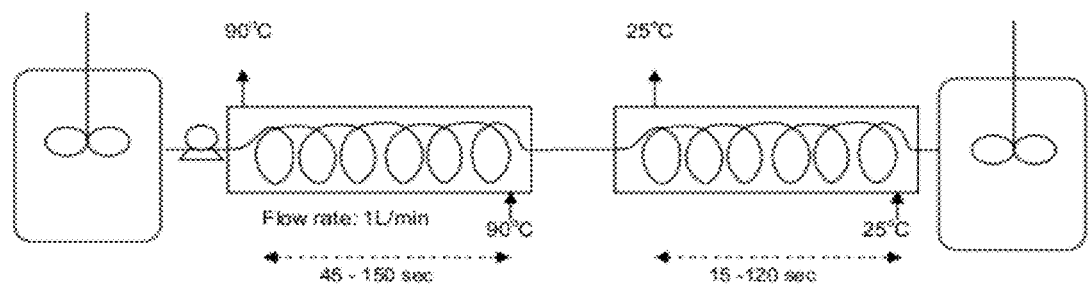
FIG. 6 is a schematic depiction of an apparatus used for HTST heat processing step.
Figure 7:
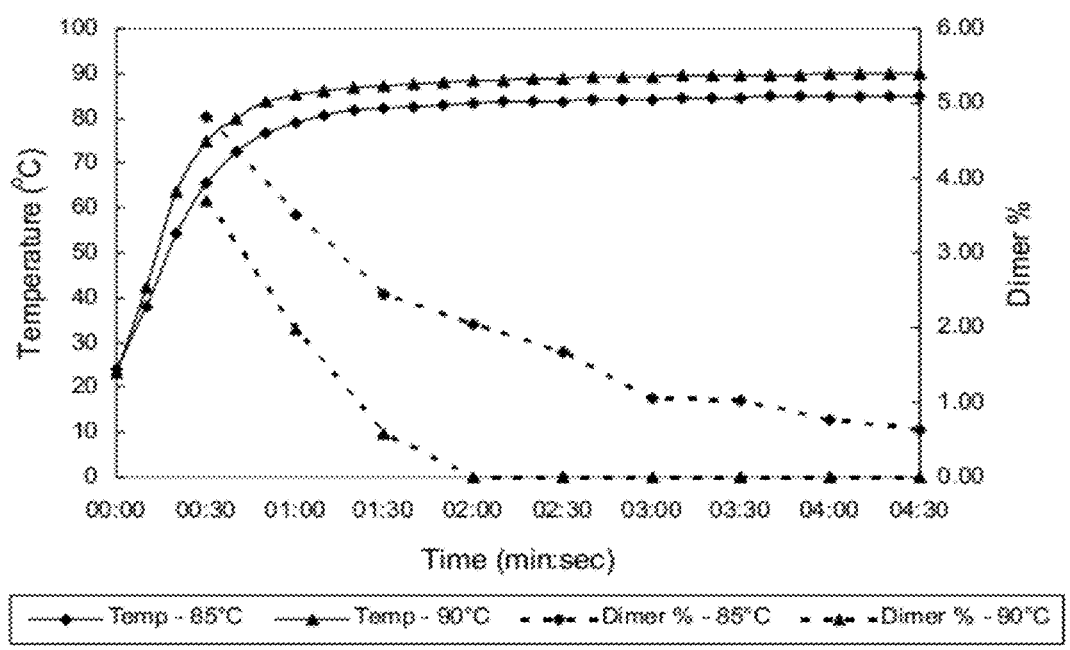
FIG. 7 demonstrates the temperature profile in the HTST processing apparatus and the time taken to remove unstabilized tetramer (dimer) in the system at 85° C. and 90° C. of the present invention.

A High Temperature Short Time (HTST) processing apparatus is shown in FIG. 6. A heat processing step using the HTST processing apparatus is performed on the crosslinked tetrameric hemoglobin. In this example, the condition for heat treatment is 90° C. for 30 seconds to 3 minutes, and preferably 45 to 60 seconds although other conditions can be selected as discussed above and the apparatus modified accordingly. A solution containing crosslinked hemoglobin optionally with 0.2% of N-acetyl cysteine added thereto is pumped into a HTST processing apparatus (first section of the HTST heat exchanger is pre-heated and maintained at 90° C.) at a flow rate of 1.0 liter per minute, the residence time of the first section of the apparatus is between 45 to 60 seconds, then the solution is passed through at the same flow rate into another section of the heat exchanger that is maintained at 25° C. The time required for cooling is between 15 to 30 seconds. After cooling down to 25° C., N-acetyl cysteine is immediately added at a concentration of 0.2% to 0.4%, preferably at 0.4%. The set-up of the heat processing apparatus is easily controlled for industrial operation. A temperature profile with dimer content is shown in FIG. 7. If the hemoglobin is not crosslinked, it is not heat stable and forms a precipitate after the heat processing step. The precipitate is then removed by a centrifugation or a filtration to form a clear solution thereafter.

The following Table 7 shows that protein impurities such as immunoglobin-G, albumin, carbonic anhydrase and undesirable non-stabilized tetramer or dimers are removed after the heat processing step. The amount of immunoglobin-G, albumin and carbonic anhydrase are measured using an ELISA method, while the amount of dimer is determined by an HPLC method. The purity of heat stable crosslinked tetrameric hemoglobin is extremely high after the HTST heat processing step, in the range of 98.0 to 100%.

TABLE 7

| Sample condition | Protein impurities (by ELISA) | | | By HPLC | |
|---|---|---|---|---|---|
| | Immuno-globin-G (µg/ml) | Albumin (µg/ml) | Carbonic anhydrase (µg/ml) | Tetramer (%) | Dimer (%) |
| No heat treatment | 0.29 | 0.52 | 261.80 | 91.8 | 5.3 |
| 90° C. for 2 min | Not detectable | 0.02 | 0.016 | 96.1 | Not detectable |
| Removal (%) | 100.0 | 96.15 | 99.99 | — | 100.0 |

Example 6

Packaging

Figure 8:
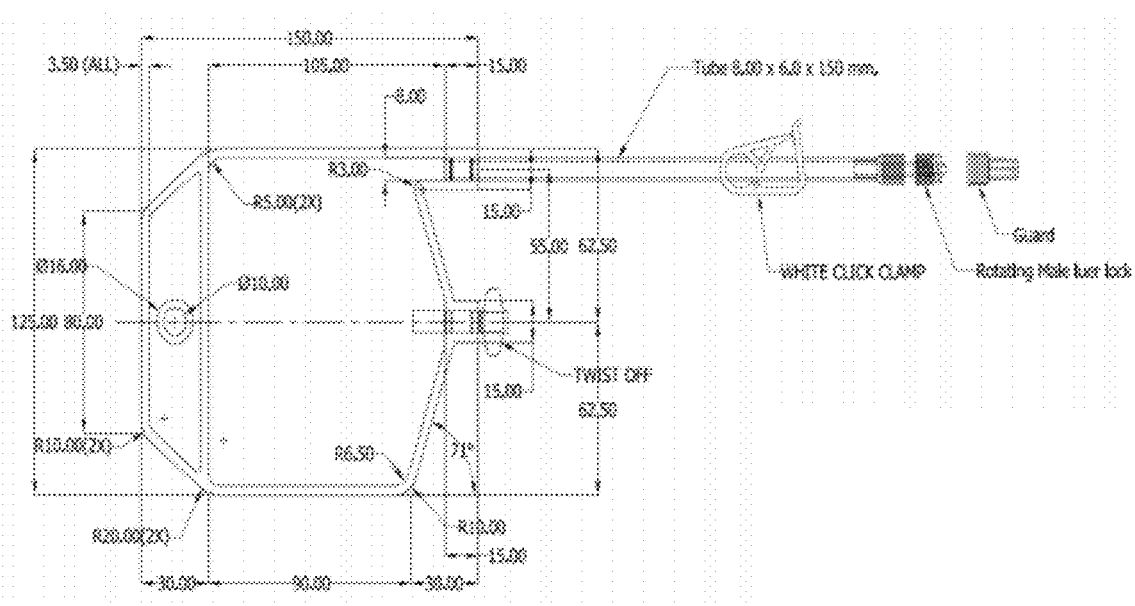
FIG. 8 is a schematic depiction of an infusion bag for the heat stable crosslinked tetrameric hemoglobin of the present invention.

Because the product of the present invention is stable under deoxygenated conditions, the packaging for the product is important to minimize gas permeability. For intravenous application, a custom designed, 100 ml infusion bag is made from a five-layer EVA/EVOH laminated material with a thickness of 0.4 mm that has an oxygen permeability of 0.006 to 0.132 $cm^3$ per 100 square inches per 24 hours per atmosphere at room temperature. This specific material is a Class VI plastic (as defined in USP<88>), which meets the in-vivo biological reactivity tests and the physico-chemical tests and are suitable for fabricating containers for intravenous injection purpose (note that other forms of packaging can be made from this material as well depending upon the desired application). A secondary packaging aluminum overwrap pouch is also applied to the primary packaging infusion bag that provides an additional barrier, minimizing light exposure and oxygen diffusion. The layers of the pouch comprise: 0.012 mm of Polyethylene terephthalate (PET), 0.007 mm of Aluminum (Al), 0.015 mm of Nylon (NY) and 0.1 mm of Polyethylene (PE). The overwrap film has a thickness of 0.14 mm and oxygen transmission rate of 0.006 $cm^3$ per 100 square inches per 24 hours per atmosphere at room temperature. A schematic depiction of the infusion bag is depicted in FIG. 8. The overall oxygen permeability for each infusion bag according to the present invention is 0.0025 $cm^3$ per 24 hours per atmosphere at room temperature.

Example 7

Characterization of Crosslinked Bovine Hb (Deoxygenated Cross-Linking Condition)

(7a) Separation of Globin Chains by Reverse Phase High Performance Liquid Chromatography (HPLC)

The globin chains of native bovine hemoglobin and crosslinked globin chains of DBSF crosslinked bovine hemoglobin are resolved on a VYDAC C4 column using the gradients developed by Shelton et al., 1984 with minor modification.

(7b) Sodium Dodecyl Sulfate Polyacrylamide Gel Electrophoresis (SDS-Page) Analysis of DBSF Crosslinked Bovine Hemoglobin Native bovine hemoglobin and DBSF crosslinked bovine hemoglobin solution are prepared by mixing with reducing sample buffer (62 mM Tris-HCl (pH 6.8), 10% (v/v) glycerol, 5% (v/v) mercaptoethanol and 2.3% (w/v) SDS), and heated at 95° C. for 10 mM The sample mixture is resolved using a 15% acrylamide slab gel with a 4% stacking gel. The electrophoresis is run with a constant current of 60 mA. After electrophoresis, the SDS-PAGE gel is stained with 0.1% (w/v) Coomassie Blue R350, 20% (v/v) methanol and 10%

(v/v) acetic acid. To estimate the percentage of different types of cross-linking in DBSF crosslinked bovine hemoglobin, the intensities of the resolved protein bands expressed in Black Light Unit (BLU) are quantified using Lumi-Analyst 3.1 Software.

(7c) Trypsin Digestion of Reduced Globin Chain

The protein band corresponding to the major crosslinked globin chain is excised from the SDS-PAGE gel, cut into cubes (1×1 mm), and de-stained with 10% methanol/10% acetic acid. The de-stained gel cubes are reduced with 10 mM DTT in 25 mM $NH_4CO_3$ and alkylated with 55 mM idoacetamide in 25 mM $NH_4CO_3$ for 45 min in dark, and then in-gel digested with 20 ng/µl modified trypsin in 25 mM $NH_4CO_3$ at 37° C. overnight. After trypsin digestion, the trypsin-digested peptides are extracted by diffusion into 50% (v/v) acetonitrile (ACN) and 1% (v/v) trifluoroacetic acid (TFA).

(7d) Matrix Assisted Laser Desorption/Ionization Time-of-Flight (MALDI-TOF) Mass Spectrometry (MS) Analysis The trypsin digested peptides extracted from the protein band are spotted onto an Anchorchip plate, which is pre-spotted with 1 µL of matrix solution (2 mg/ml cyano-4-hydroxycinnamic acid, saturated in 50% ACN/0.1% TFA, and allowed to air-dry. After drying, the sample spot is washed with 10 mM monophosphate buffer and recrystallized using a solution of ethanol: acetone: 0.1% TFA (6:3:1 ratio). MALDI-TOF MS analysis is performed with a Bruker Autoflex III (Bruker Daltonic GmbH, Bremen, Germany) operated in the reflectron mode over the m/z range of 800-3500 Da and the parameters are set as follows: ion source 25 kV for peptide mass fingerprint (PMF), and reflector 26.3 kV for PMF. External calibration is performed using a Bruker Peptide Mix Calibration Standard. The peaks with a S/N ratio over 4 are automatically labeled by Flex-Analysis (Bruker Daltonic GmbH, Bremen, Germany) The MS data is further analyzed through MASCOT 2.2.04 and Biotools 2.1 software (Bruker Daltonic GmbH, Bremen, Germany), and these data were searched against Mammalian proteins in NCBI nonredundant (NCBInr) database. The following parameters are used for database searches: monoisotopic mass accuracy <250 ppm, parent charge +1, missed cleavages 1, carbamidomethylation of cysteine as fixed modification, oxidation of methionine as variable modification.

(7e) Liquid Chromatography-Electrospray Ionization (LC-ESI) Tandem Mass Spectrometry (MS/MS) Analysis Nano-LC MS/MS analysis of the trypsin digested peptides from the protein band is performed using a capillary HPLC coupled directly to HCT Ultra ESI– ion trap mass spectrometer (Bruker Daltonic GmbH, Bremen, Germany) Peptide digests are dissolved in 0.1% formic acid/2% ACN prior to column injection. A gradient from 4-90% (0.001% formic acid and 0.001% formic acid in 80% ACN) is used for peptide separation using a C18 column (15 cm×75 nm, LC PACKINGS). The flow rate is 250 ng/min at 25° C. Eluates from a C18 column are entered into the HCT Ultra ESI– ion trap mass spectrometer, operated in linear mode for online analysis. The ion trap mass spectrometer is optimized with the nanosource with a spray voltage of 137V and a heated capillary temperature of 160° C. The accumulation time for peptide ions in the ion trap is set to be 200 ms, and the mass to charge ratio selected for MS/MS analysis is from 100 to 1800 Da with a charge state 1-3.

Figure 9:
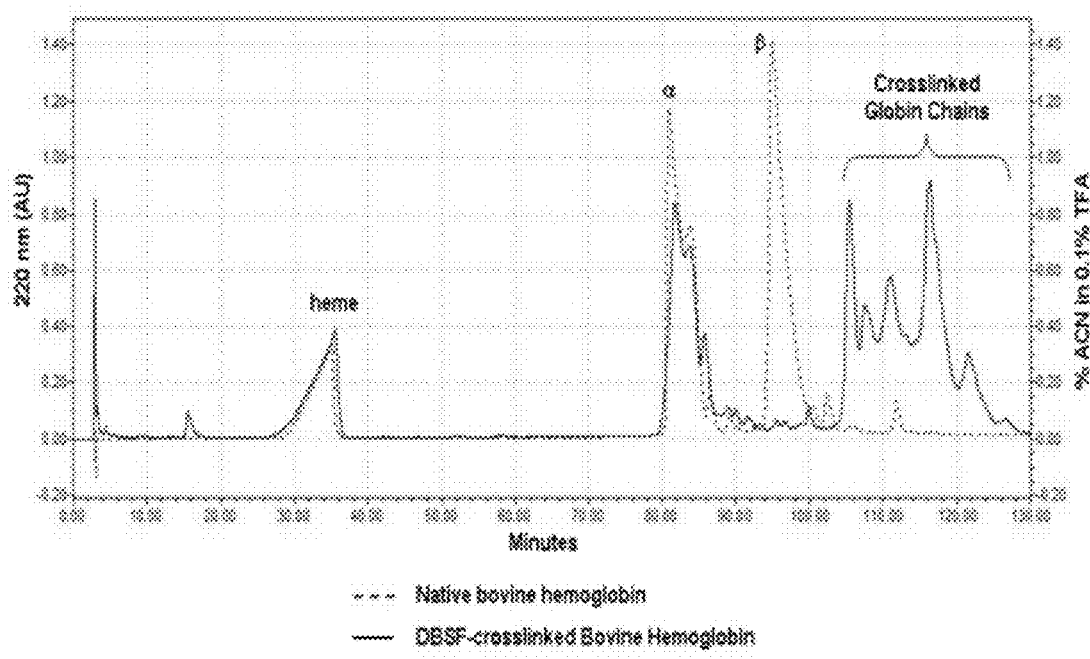
FIG. 9 depicts reverse phase HPLC chromatogram of α and β globin chains of bovine hemoglobin before (dashed line) and after (solid line) reaction with DBSF under deoxygenated environment.
Figure 10:
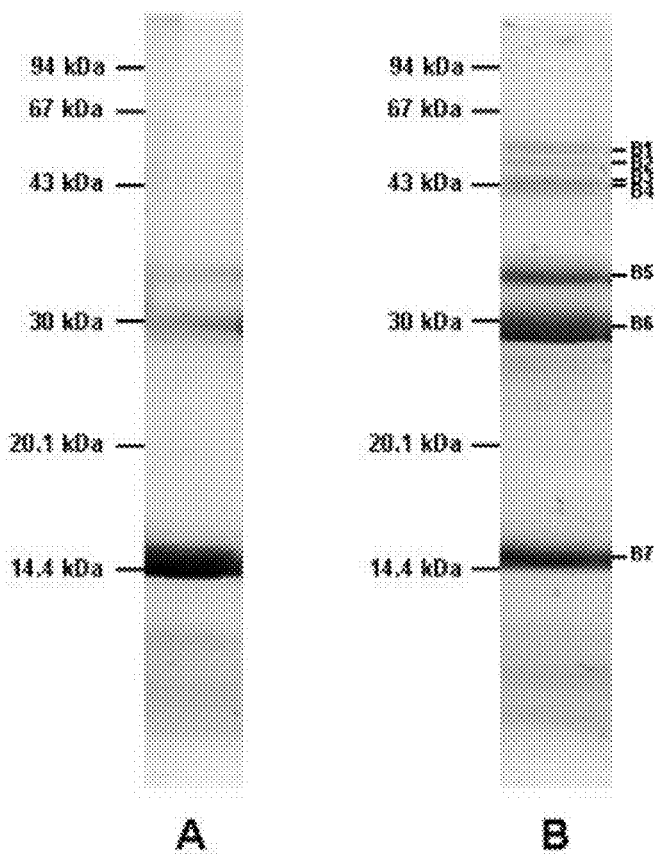
FIG. 10 depicts 15% SDS-PAGE analysis of (A) native bovine hemoglobin and (B) hemoglobin crosslinked with DBSF under deoxygenated condition.
Figure 11:
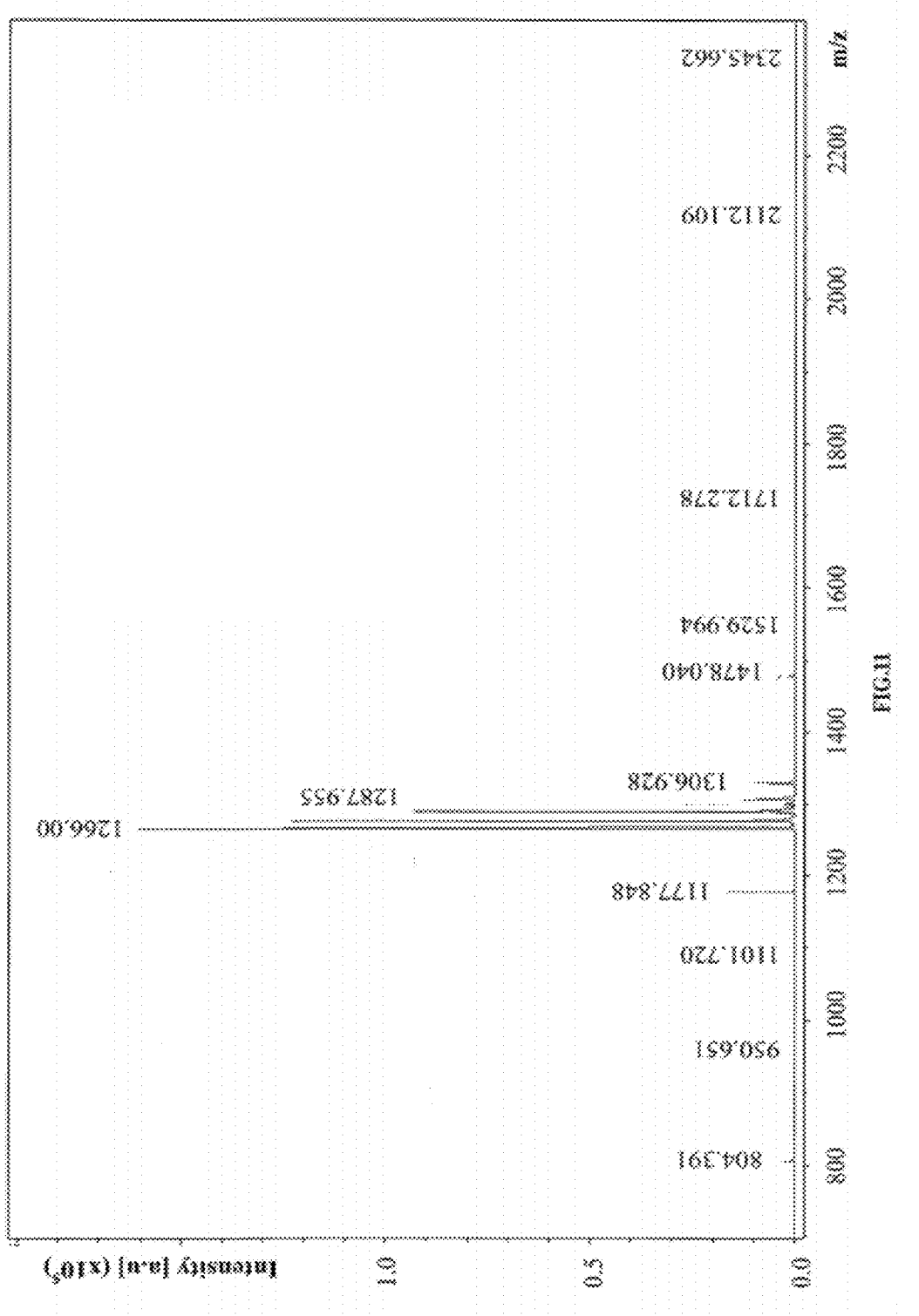
FIG. 11 depicts the peptide mass fingerprint of trypsin-digested peptides from the dimeric protein band (B6) generated by MALDI-TOF analysis.

The reverse phase HPLC on a VYDAC C4 column, monitored at a wavelength of 220 nm, is employed to separate different types of cross-linking occurring between α and β chains in the DBSF crosslinked bovine hemoglobin. The chromatographic patterns obtained using bovine hemoglobin before and after cross-linking with DBSF are shown in FIG. 9. In FIG. 9, the α chains are more mobile than the β chains of native bovine hemoglobin (as shown with dashed line). Their identities are confirmed by MALDI-TOF analysis. After the reaction with DBSF, the β chains are crosslinked while a large majority of α chains are left alone (as shown with solid line). As a consequence of cross-linking with DBSF, 6 major globin peaks with greater hydrophobicity than the native β chains are formed. The crosslinked globin chains in the DBSF crosslinked bovine hemoglobin are also resolved by 15% SDS-PAGE, as shown in FIG. 10. The major crosslinked globin chain (B6 in FIG. 10) is subjected to trypsin digestion and subsequent MALDI-TOF analysis, and it is identified as beta globin chain only, based on its peptide mass fingerprint, as shown in FIG. 11.

While the foregoing invention has been described with respect to various embodiments, such embodiments are not limiting. Numerous variations and modifications would be understood by those of ordinary skill in the art. Such variations and modifications are considered to be included within the scope of the following claims.

What is claimed:

1. A method for the preparation of a highly purified and heat stable oxygen carrier-containing pharmaceutical composition, the oxygen carrier-containing pharmaceutical composition including hemoglobin, the hemoglobin consisting essentially of non-polymeric crosslinked tetrameric hemoglobin having a beta-beta cross-linking of greater than 40%, the method comprising:

a) providing mammalian whole blood including at least red blood cells and plasma;

b) separating the red blood cells from the plasma in the mammalian whole blood;

c) filtering the red blood cells that were separated from the plasma to obtain a filtered red blood cell fraction;

d) washing the filtered red blood cell fraction to remove plasma protein impurities, resulting in washed red blood cells;

e) disrupting the washed red blood cells to create a solution comprising a lysate of disrupted red blood cells;

f) performing filtration to remove at least a portion of the waste retentate from the lysate;

g) extracting a first hemoglobin solution from the lysate;

h) performing at least one purification process to remove one or more of viruses, waste retentate, or protein impurities;

i) cross-linking the first hemoglobin solution by bis-3,5-dibromosalicyl fumarate to form crosslinked hemoglobin in an oxygenated environment wherein the crosslinked hemoglobin is non-polymeric crosslinked tetrameric hemoglobin having at least 40% beta-beta cross-linking;

j) removing any residual chemicals;

k) heat treating the crosslinked hemoglobin in a deoxygenated environment to denature and precipitate any residual non-stabilized/non-crosslinked hemoglobin, any dimeric hemoglobin and any other protein impurities such that the resulting heat stable crosslinked tetrameric hemoglobin has an undetectable concentration of dimer and consists essentially of non-polymeric crosslinked tetrameric hemoglobin with a beta-beta cross-linking of at least 40% and an oxygen affinity greater than the oxygen affinity of native hemoglobin of the same species measured under substantially similar conditions;

l) removing precipitate by a centrifugation or a filtration to form a clear solution; and m) adding the purified and heat stable crosslinked tetrameric hemoglobin to a pharmaceutically acceptable carrier.

2. The method for the preparation of a highly purified and heat stable oxygen carrier-containing pharmaceutical composition according to claim 1 wherein the heat processing step is a high temperature short time (HTST) process conducted at approximately 70° C. to 95° C. for 30 seconds to 3 hours followed immediately by cooling and adding N-acetyl cysteine in an amount of 0.2 to 0.4% immediately following the cooling.

3. The method for the preparation of a highly purified and heat stable oxygen carrier-containing pharmaceutical composition according to claim 1 wherein the whole blood is bovine whole blood and the beta-beta cross-linking is greater than 50% and the p50 value is less than approximately 23 mm Hg.

4. The method for the preparation of a highly purified and heat stable oxygen carrier-containing pharmaceutical composition according to claim 1 wherein the whole blood is bovine whole blood and the beta-beta cross-linking is greater than 60% and the p50 value is less than approximately 23 mm Hg.

5. The method for the preparation of a highly purified and heat stable oxygen carrier-containing pharmaceutical composition according to claim 1 wherein the purification is performed using chromatography, the chromatography including use of one or more cation-exchange columns or anion-exchange columns.

6. The method for the preparation of a highly purified and heat stable oxygen carrier-containing pharmaceutical composition according to claim 5 wherein the chromatography column is one or more DEAE, CM and/or hydroxyapatite columns.

7. The method for the preparation of a highly purified and heat stable oxygen carrier-containing pharmaceutical composition according to claim 1 wherein the whole blood is human blood.

8. The method for the preparation of a highly purified and heat stable oxygen carrier-containing pharmaceutical composition according to claim 1 wherein the whole blood is porcine blood, equine blood, or canine blood.

9. A method for the preparation of a highly purified and heat stable oxygen carrier containing pharmaceutical composition according to claim 1 further comprising packaging the hemoglobin solution in a low oxygen permeability package such that hemoglobin solution has a shelf life on the order of two years.

10. A method for the preparation of a highly purified and heat stable oxygen carrier-containing pharmaceutical composition, the oxygen carrier-containing pharmaceutical composition including hemoglobin, the hemoglobin consisting essentially of non-polymeric crosslinked tetrameric hemoglobin having a beta-beta cross-linking of greater than 50%, the method comprising:
a) providing mammalian whole blood including at least red blood cells and plasma;
b) separating the red blood cells from the plasma in the mammalian whole blood;
c) filtering the red blood cells that were separated from the plasma to obtain a filtered red blood cell fraction;
d) washing the filtered red blood cell fraction to remove plasma protein impurities, resulting in washed red blood cells;
e) disrupting the washed red blood cells to create a solution comprising a lysate of disrupted red blood cells;
f) performing filtration to remove at least a portion of the waste retentate from the lysate;
g) extracting a first hemoglobin solution from the lysate;
h) performing at least one purification process to remove one or more of viruses, waste retentate, or protein impurities;
i) cross-linking the hemoglobin by bis-3,5-dibromosalicyl fumarate to form crosslinked hemoglobin in a deoxygenated environment wherein the crosslinked hemoglobin is non-polymeric crosslinked tetrameric hemoglobin having at least 50% beta-beta cross-linking;
j) removing any residual chemicals;
k) heat treating the crosslinked hemoglobin in a deoxygenated environment to denature and precipitate any residual non-stabilized/non-crosslinked hemoglobin, any dimeric hemoglobin and any other protein impurities such that the resulting heat stable crosslinked tetrameric hemoglobin has an undetectable concentration of dimer and consists essentially of non-polymeric crosslinked tetrameric hemoglobin with a beta-beta cross-linking of at least 50% having an oxygen affinity less than the oxygen affinity of native hemoglobin of the same species measured under substantially similar conditions;
l) removing precipitate by a centrifugation or a filtration to form a clear solution; and
m) adding the purified and heat stable crosslinked tetrameric hemoglobin to a pharmaceutically acceptable carrier.

11. The method for the preparation of a highly purified and heat stable oxygen carrier-containing pharmaceutical composition according to claim 10 wherein the whole blood is bovine whole blood and the oxygen affinity of the crosslinked tetrameric bovine hemoglobin has a p50 value on the order of approximately 38 to 50 mm Hg.

12. A method for the preparation of a highly purified and heat stable oxygen carrier containing pharmaceutical composition according to claim 10 further comprising packaging the hemoglobin solution in a low oxygen permeability package such that hemoglobin solution has a shelf life on the order of two years.

* * * * *